US006231563B1

(12) United States Patent
White et al.

(10) Patent No.: US 6,231,563 B1
(45) Date of Patent: May 15, 2001

(54) DIRECTIONAL CATHETER

(75) Inventors: Geoffrey H. White, East Balmain; Weiyun Yu, Five Dock, both of (AU); Mark Dehdashtian, Costa Mesa, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/117,092

(22) PCT Filed: Jan. 28, 1997

(86) PCT No.: PCT/AU97/00046

§ 371 Date: Apr. 14, 1999

§ 102(e) Date: Apr. 14, 1999

(87) PCT Pub. No.: WO97/26936

PCT Pub. Date: Jul. 31, 1997

(30) Foreign Application Priority Data

Jan. 25, 1996 (AU) ................................................. PN 7752

(51) Int. Cl.[7] ................................................. A61M 25/00
(52) U.S. Cl. ........................... 604/523; 604/284; 604/528
(58) Field of Search .................................. 604/528, 530, 604/525, 158, 161, 163, 284, 164, 95; 606/194; 206/570

(56) References Cited

U.S. PATENT DOCUMENTS

| 4,548,597 | 10/1985 | Nelson . |
| 4,552,554 | 11/1985 | Gould et al. . |
| 4,769,005 | 9/1988 | Ginsburg et al. . |
| 5,030,204 | * 7/1991 | Badger et al. .................... 604/523 X |
| 5,059,177 | * 10/1991 | Towne et al. ........................... 604/96 |
| 5,064,435 | 11/1991 | Porter . |
| 5,300,048 | * 4/1994 | Drewes, Jr. et al. ............ 604/530 X |
| 5,397,345 | 3/1995 | Lazarus . |
| 5,413,581 | 5/1995 | Goy . |
| 5,443,497 | 8/1995 | Venbrux . |
| 5,489,295 | 2/1996 | Piplani et al. . |
| 5,522,880 | 6/1996 | Barone et al. . |
| 5,562,726 | 10/1996 | Chuter . |
| 5,562,728 | 10/1996 | Lazarus et al. . |
| 5,575,817 | 11/1996 | Martin . |
| 5,591,228 | * 1/1997 | Edoga ............................... 606/198 X |
| 5,609,605 | 3/1997 | Marshall et al. . |
| 5,676,696 | 10/1997 | Marcade . |
| 5,676,697 | 10/1997 | McDonald . |
| 5,683,449 | 11/1997 | Marcade . |
| 5,683,453 | 11/1997 | Palmaz . |
| 5,797,949 | 8/1998 | Parodi . |
| 5,824,039 | 10/1998 | Piplani et al. . |
| 5,824,055 | 10/1998 | Spiridigliozzi et al. . |
| 5,871,536 | 2/1999 | Lazarus . |

FOREIGN PATENT DOCUMENTS

| 53696/94 | 5/1995 | (AU) . |
| WO 95/04567 | 2/1995 | (WO) . |
| WO 95/24235 | 9/1995 | (WO) . |
| WO 96/11648 | 4/1996 | (WO) . |

* cited by examiner

Primary Examiner—Wynn Wood Coggins
Assistant Examiner—A. T. Nguyen
(74) Attorney, Agent, or Firm—Baxter Healthcare Co Vasc. Sys. Div.; Peter Jon Gluck; B. M. Canter

(57) ABSTRACT

An intraluminal catheter for directing a guidewire and/or catheter in a desired direction within a bodily vessel or cavity. The intraluminal catheter has a first elongate tubular member and a support means which can comprise a second elongate tubular member that can pass over a main support guidewire. The catheter acts as a platform as the guidewire is passed through the first elongate tubular member and is deflected transversely outwardly by an angled surface through an aperture. A second intraluminal catheter has a first elongate tubular member and a support means comprising a second elongate tubular member. The first elongate tubular member has a main portion and an end portion, with the end portion being deflectable relative to the locus of the main portion so as to direct the guidewire passing through the end portion in a desired direction in the bodily vessel.

2 Claims, 10 Drawing Sheets

DIRECTIONAL CATHETER

FIELD OF THE INVENTION

The present invention relates to catheters and particularly to directional catheters for use in medical applications.

BACKGROUND ART

The placement of prosthetic devices, such as stents and grafts, intraluminally and the conduct of operative procedures intraluminally has grown dramatically in recent years. In many of these placements and procedures, it is necessary to initially position a guidewire into a desired part of the lumen of a desired vessel or duct, such as a blood vessel. Once an initial guidewire is in place, a catheter or other tubular device may be positioned over the guidewire and used to convey another guidewire, a prosthesis, an endoscope or a surgical instrument into the desired blood vessel or duct.

There are a variety of techniques used to position guidewires in branching vessels intraluminally. One technique is to position a relatively stiff guidewire in a bodily vessel and then to pass over it a catheter having a region proximate its tip that normally assumes an angled, curved or some other configuration. On positioning the catheter over the stiff guidewire in the necessary position, the stiff guidewire is withdrawn allowing the region near the tip of the catheter to assume its normal configuration. A thin guidewire can then be fed through the catheter and directed in the direction assumed by the catheter. The thin guidewire is preferably sufficiently floppy that it is directed by the catheter in the direction assumed by the catheter rather than causing the catheter to adopt the configuration of the thin guidewire. As the first stiff guidewire must firstly be removed to allow the insertion of the thin guidewire, it is clinically undesirable to re-insert the stiff guidewire if required at a later time. Further, withdrawal of the stiff guidewire leads to there being no control over the position assumed by the catheter and it is common for the catheter to assume an undesirable position thereby requiring re-insertion of the stiff guidewire to correct the situation. The strength of the catheter further limits the stiffness of the thin guidewire or another secondary catheter that may be subsequently inserted through the catheter which can lead to further complications in successfully positioning a guidewire through the branching bodily vessel.

One example of a guiding catheter is described in U.S. Pat. No. 4,898,577 to Badger et al. The Badger guiding catheter comprises a single elongated shaft having a deflectable distal portion, the angle of deflection of the distal portion relative to the elongated shaft being controlled by a pull wire that extends from the distal portion back through a lumen to a proximal end of the catheter where it can be controlled by a physician. Once the distal portion is at the required deflection, the guidewire is fed through the catheter.

Another type of directable catheter is the so-called torquable catheter, an example of which is described in Australian Patent Specification AU-A-32951/95 to Lundquist. The Lundquist catheter once again has a single elongated shaft which has a flexible portion which can bend under the control of a physician to deflect the end of the catheter and so direct a guidewire passing therethrough in a desired direction.

Even with directable or torquable catheters, physicians still often encounter problems in achieving desired placement of guidewires and catheters in bodily vessels. Problems are especially encountered when it is necessary to direct a guidewire into a vessel branching of the main vessel. Conversely, problems also arise of a guidewire undesirably entering a branching vessel instead of remaining in the main vessel.

One example where it is often necessary to direct a guidewire into a branching vessel is in the placement of an intraluminal graft into a patient to achieve bridging and occlusion of an aneurysm of the aorta, iliac or other arteries. The present invention is directed to an alternative directional catheter which can be used for the intraluminal placement of a guidewire or catheter in a bodily vessel or cavity.

DISCLOSURE OF THE INVENTION

The present inventors have determined that substantial advantages over traditional techniques can be gained by positioning a main guidewire in a bodily vessel and then using that guidewire as a platform to insert and support a catheter, which catheter can be used to direct a supplementary guidewire and/or catheter in a direction transverse to the locus of the main guidewire.

Accordingly, in a first aspect, the present invention consists in an intraluminal catheter for insertion through a bodily vessel, the catheter having a first elongate tubular member defining a first lumen, the tubular member having a main portion and on its outer surface a support means adapted to slide over a main guidewire positioned in the vessel, the first elongate tubular member having an end portion that is deflectable relative to the locus of the main portion to direct a supplementary guidewire passing through the first lumen into the bodily vessel in a direction transverse to the locus of the main guidewire The provision of the support means on the intraluminal catheter allows the intraluminal catheter to be supported on the main guidewire already positioned in a bodily vessel as the supplementary guidewire is fed through the first lumen. The use of such a catheter removes the need to withdraw the stiff guidewire before insertion of the supplementary guidewire. Further, the support during deployment of the supplementary guidewire ensures the guidewire is deployed in a direction desired by the physician transverse to the locus of the main guidewire.

In one embodiment, the support means can comprise a second elongate tubular member in side-by-side configuration with the first tubular member. The second tubular member can be at least as long as the first elongate tubular member. The catheter can also have a third or further number of lumens.

The end portion can have a surface angled to the locus of the first lumen or an extension thereof such that the supplementary guidewire on passing through the first lumen will strike the angle surface and be further deflected laterally out of the locus of the first lumen or the extension thereof. The angled surface is preferably positioned within the first lumen with the first tubular member having an aperture opposite the angled surface such that the supplementary catheter on passing through the first lumen is deflected by the angled surface through the aperture. The angled surface can be proximate a free end of the first tubular member.

In another embodiment, the catheter can further comprise a means to control the deflection of the end portion relative to the locus of the main portion.

In a further embodiment the controlling means can comprise a control wire that extends along the catheter and is secured to the end portion with retraction of the control wire relative to the catheter deflecting the end portion relative to the locus of the main portion. If desired, the control wire can be disposed within a further lumen of the catheter.

The main portion of the first tubular member can normally assume a straight configuration and the end portion can normally assume a curved configuration, the catheter further having a sleeve that is relatively movable longitudinally with respect to the first tubular member between a first position where the sleeve surrounds the end portion and so straightens the end portion and a second retracted position where the end portion is free to assume its normal curved configuration.

In this specification, the normal configuration of the first tubular member according to the present invention is taken to be configuration adopted by the tubular member when the catheter is outside the body and the sleeve is in the second retracted position relative to the first tubular member.

In another embodiment, the main portion can normally assume a straight configuration and the end portion can be preformed at an angle to the main portion, the catheter further having a sleeve that is relatively movable longitudinally with respect to the first tubular member between a first position where the sleeve surrounds the end portion and so straightens the end portion and a second retracted position where the end portion is free to assume its preformed angle to the main portion.

The end portion of the catheter is preferably fabricated from a shape memory material that will adopt the normally curved or angled configuration when the catheter is in the desired position in the bodily vessel and the sleeve is retracted relative to the first tubular member.

The catheter is preferably dimensioned such that it can be introduced into the bodily vessel through an 18 French introducer sheath.

According to a second aspect, the present invention comprises a kit for directing a supplementary guidewire in a direction transverse to the locus of a main guidewire positioned in a bodily vessel, the kit comprising an intraluminal catheter having a first elongate tubular member having a first lumen, the tubular member having a main portion and a support means on its outer surface adapted to slide over the main guidewire positioned in the bodily vessel, the supplementary guidewire being positioned in the first lumen, and the first tubular member having an end portion that is deflectable relative to the locus of the main portion to direct the supplementary guidewire passing through the first lumen in the transverse direction.

In one embodiment of the second aspect, a supplementary catheter can be positioned over the supplementary guidewire in the first lumen. The supplementary catheter can have a distal steerable end, an end portion that has a preformed angle, or can normally assume a curved configuration. In another embodiment, the supplementary catheter can have the features of the intraluminal catheter according to the first, second or third aspects of the present invention.

According to a further aspect, the present invention comprises a method for directing a supplementary guidewire in a direction transverse to the locus of a main guidewire positioned in a bodily vessel, comprising the steps of:
(a) positioning the main guidewire in the bodily vessel;
(b) guiding the support means of the intraluminal catheter as defined herein over the main guidewire and into the bodily vessel;
(c) passing the supplementary guidewire through the first lumen of the intraluminal catheter so that it is directed by the deflectable end portion in the transverse direction into the bodily vessel.

In a preferred embodiment of this aspect, a supplementary catheter is firstly passed through the first lumen so that it is directed in the transverse direction and the supplementary guidewire is then passed through the supplementary catheter. The supplementary guidewire is preferably directed into a vessel branching off the bodily vessel.

BRIEF DESCRIPTION OF THE DRAWINGS

Hereinafter by way of example only, preferred embodiments of the invention are described with reference to the accompanying drawings, in which.

PREFERRED MODE OF CARRYING OUT THE INVENTION

The present invention can be used in any surgical procedure where it is necessary to direct a guidewire into a bodily vessel whether it be for the placement of an intraluminal graft or another surgical procedure. Examples of vessels in which it can be necessary to direct a guidewire include the aorta, the renal and the iliac arteries.

The present invention is hereinafter described with reference to the example of the placement of an intraluminal graft into a patient to achieve bridging and occlusion of an aortic aneurysm. Other examples of where the present invention will have application will be readily apparent to persons skilled in the art.

Figure 1:
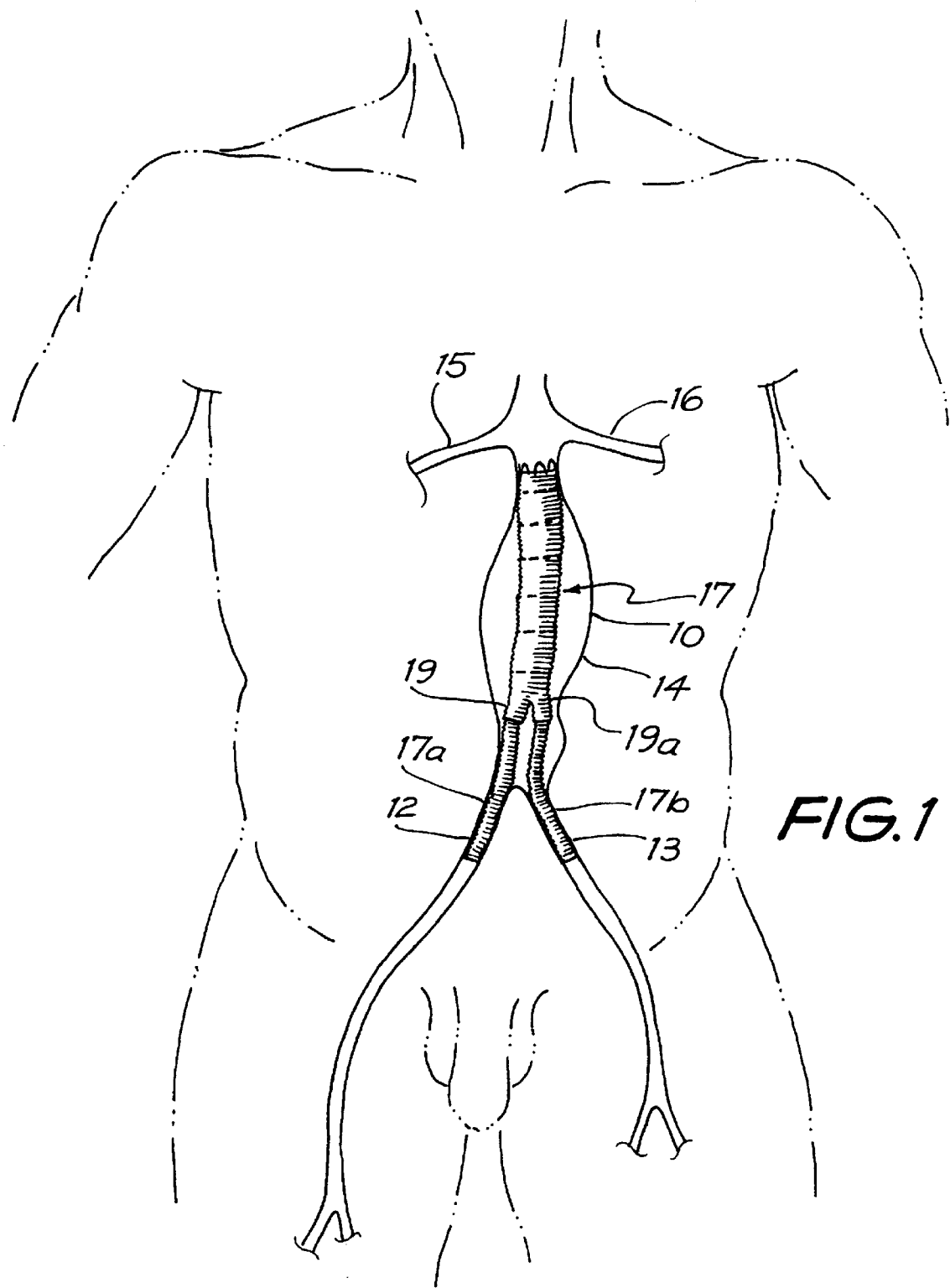
FIG. 1 is a diagrammatic representation of a ventral view of a patient having an aortic aneurysm bridged by a trouser graft.

As is seen in FIG. 1, the aorta 10 branches into the right and left iliac arteries 12,13. The aortic aneurysm 14 is located between the renal arteries 15,16 and extends down the left iliac artery 13. One means of bridging the aneurysm 14 is to use a trouser graft 17 which is provided with a bifurcation to form a pair of short tubular extensions 19,19a which are connected to tubular grafts 17a,17b which extend down the iliac arteries 12,13, respectively. One such trouser graft is described in Australian Patent Specification No AU-A-78035/94, the description of which is incorporated herein by reference.

The method for positioning an intraluminal graft will now be described with reference to FIGS. 2a–i. In carrying out the method an incision is made to expose one of the femoral arteries (ipsilateral), which flows from the corresponding iliac artery, and using the Seldinger needle technique, a 0.035" diameter floppy tipped flexible guidewire is inserted into and through the femoral artery and then the iliac artery 12 into the aorta 10 such that it traverses the aneurysm 14. An 8 French haemostatic sheath is then introduced over the wire to control bleeding. An angiographic catheter is then introduced to allow an angiogram to be taken of the patient to show the position of the renal arteries 15,16 and other relevant anatomical structures in the patient.

An Amplatz extra stiff AES guidewire 23 (0.035" diameter) is then passed through the angiographic catheter into the aorta 10. After withdrawal of the angiographic catheter, the stiff guidewire 23 is left in situ. A sheath 21, preferably of 18 French, is then introduced into the aorta 10 over the stiff guidewire 23 (see FIG. 2a). A balloon catheter 24 is then introduced into the sheath 21 over the stiff guidewire 23.

Figure 3:
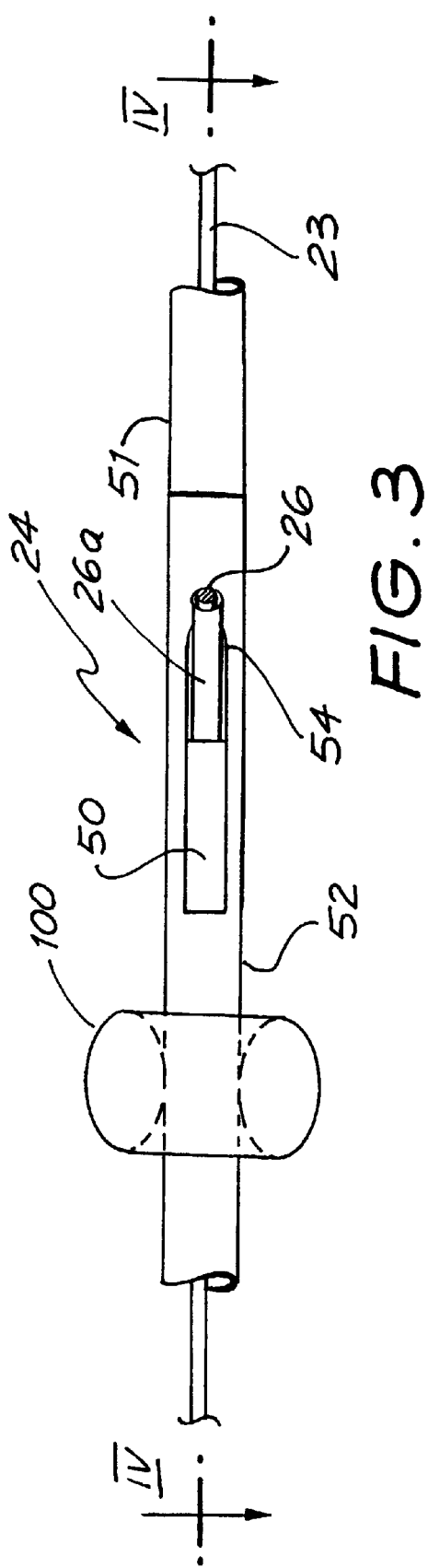
FIG. 3 is a side elevational view of the end portion of one embodiment of an intraluminal catheter according to the present invention.
Figure 9:
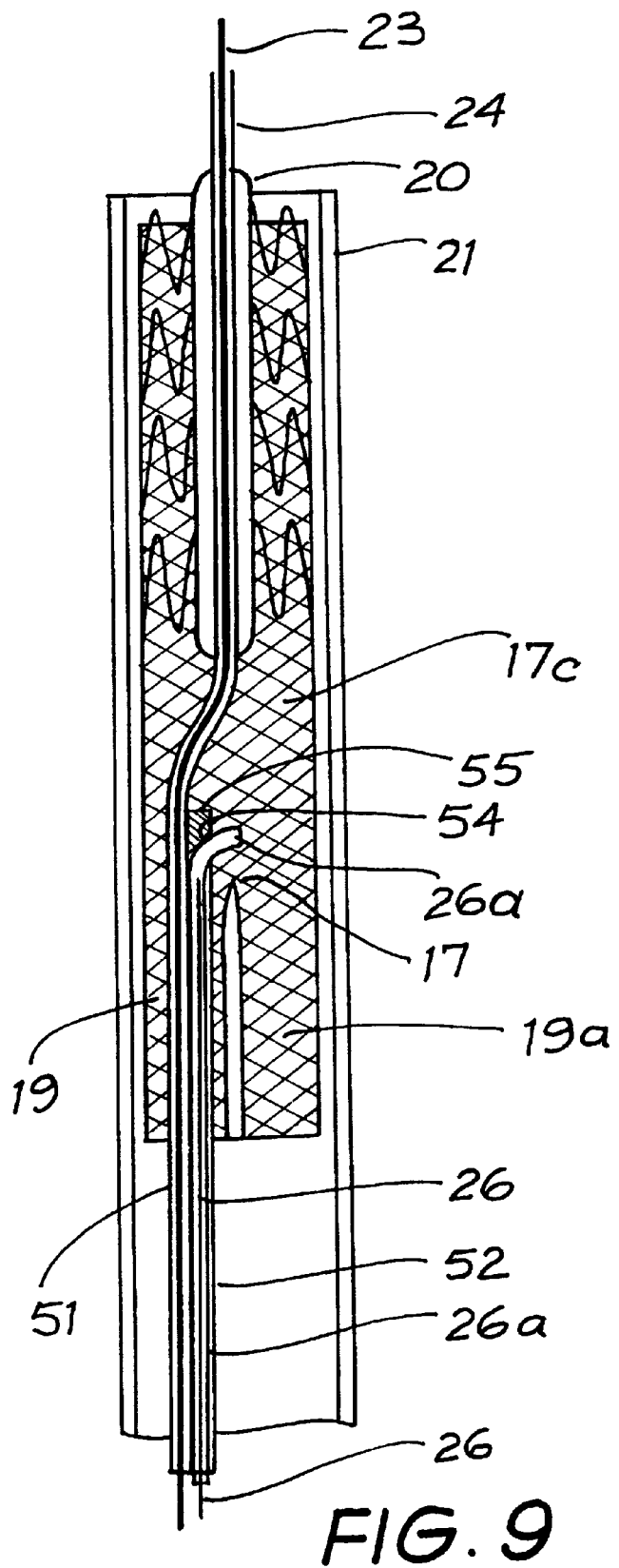
FIG. 9 is a vertical sectional view of one embodiment of a possible bifurcated graft mounted over a delivery catheter for use in the method depicted in FIGS. 2a–i.

As is seen in FIG. 9, the balloon catheter 24 is prepackaged with a bifurcated graft 17, having a bifurcation point 17c, an ipsilateral extension 19, and a contralateral extension 19a. As is seen in more detail in FIGS. 3 and 4, the catheter 24 has a first elongate tubular member 52 and a second elongate tubular member 51 that is adapted to pass over the stiff guidewire 23 and support the catheter 24 within the intraluminal graft 17. Disposed within the first tubular member 51 is a supplementary guidewire 26 surrounded by a thin supplementary catheter sheath 26a that extends in a first direction up the ipsilateral extension 19, with the end 55 of the first tubular member 52 being disposed just above the bifurcation point 17c.

Figure 2B:
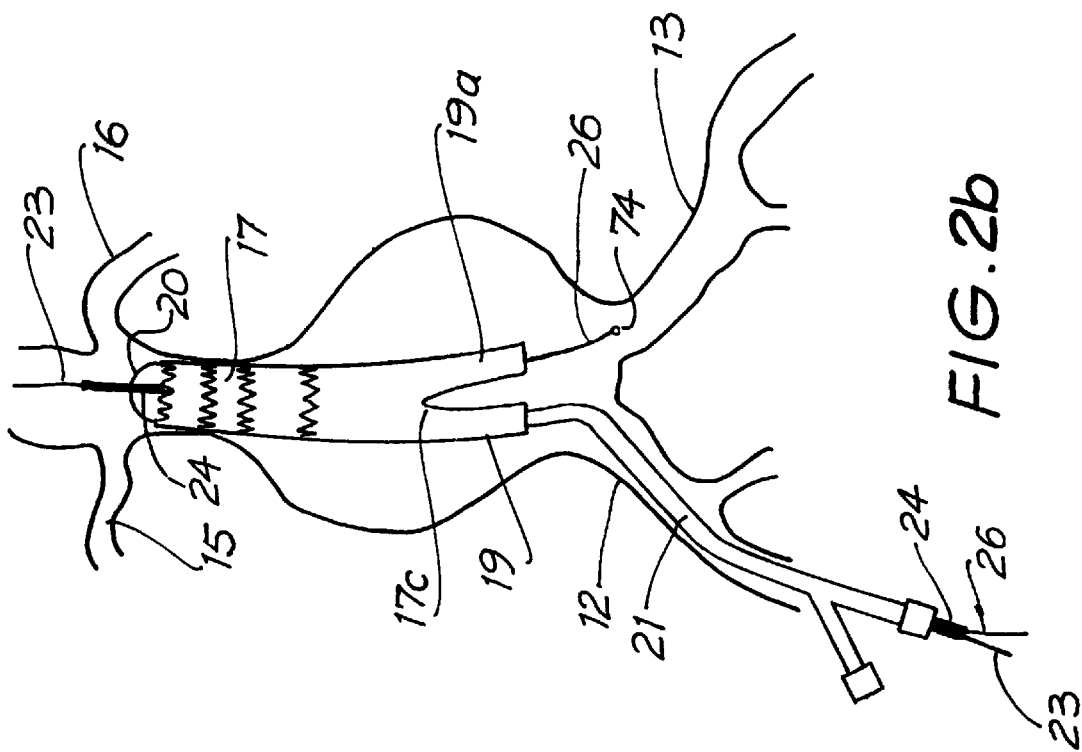
FIGS. 2a–i show the stages of carrying out a method of intraluminally placing a trouser graft into a patient which in part uses the invention defined herein.
Figure 2A:
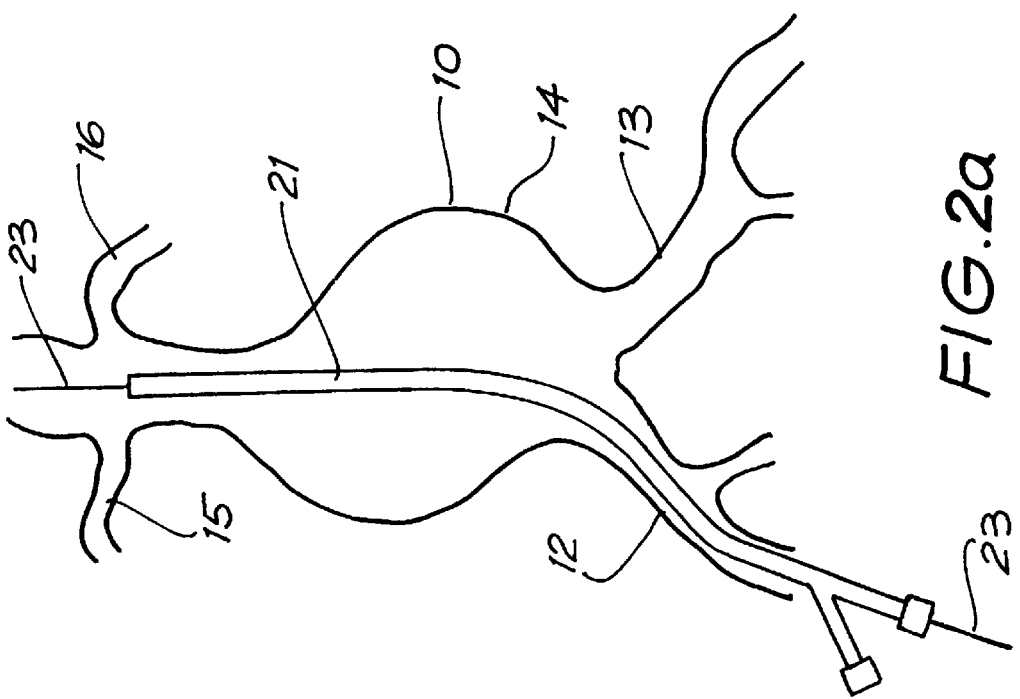
Figure 2D:
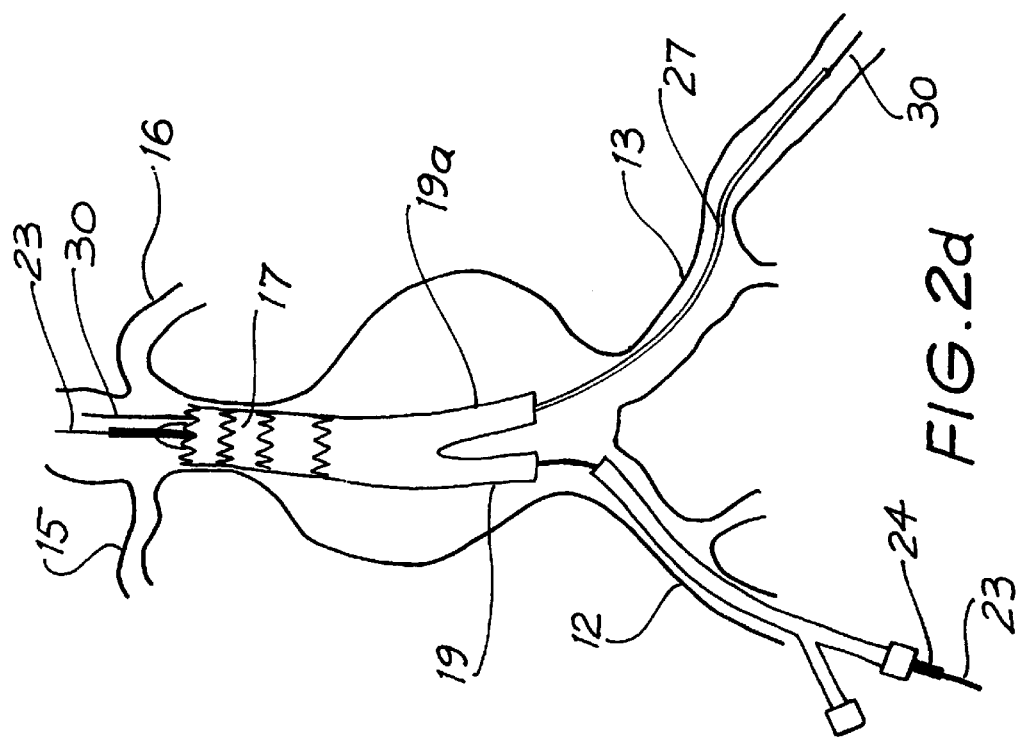

When the balloon catheter 24 is positioned within the aorta 10 correctly, the sheath 21 is partially withdrawn to free the graft 17 so that the balloon 20 may be inflated (see FIG. 2b). The inflation of the balloon 20 expands the upstream end of the first graft 17 and causes it to engage its upstream end against the aorta wall above the aneurysm 14 but downstream of the renal arteries 15,16. The first graft 17 is of such a length that the short tubular extensions 19,19a are disposed wholly within the aorta 10. The balloon 20 is then deflated but the balloon catheter 24 is left in place for the time being (see FIG. 2c). Deflation of the balloon 20 allows blood to flow down and distend the graft 17 and the tubular extensions 19,19a.

Once the first graft 17 is in place, it is necessary to extend the guidewire 26 down the left iliac artery 13. In the depicted example, this is achieved by guiding the supplementary catheter 26a through the lumen of the first tubular member 52 such that it strikes the angled surface 54 and is deflected laterally out of the locus of the first tubular member 52 and through the aperture 50 in the first tubular member opposite the angled surface 54. The region of the catheter 26a proximate its tip can normally assume an angle or curved configuration relative to the normally straight configuration of the remainder of the catheter 26a.

Figure 2C:
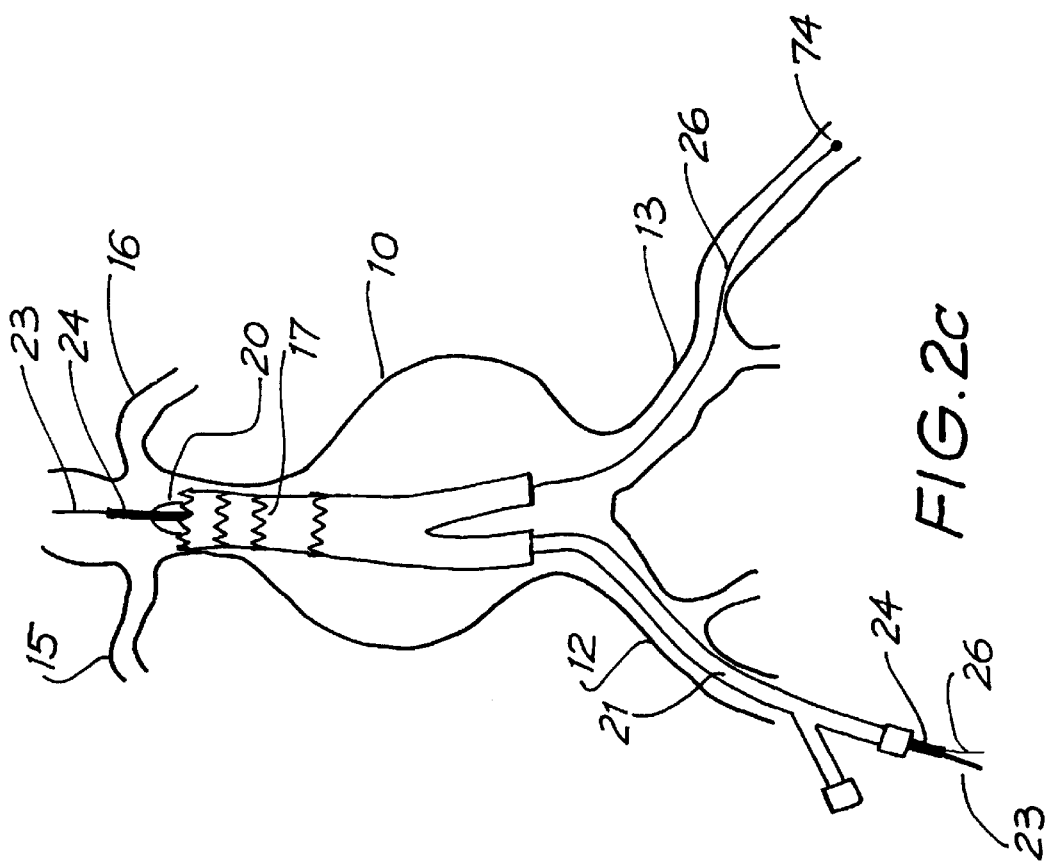
Figure 2F:
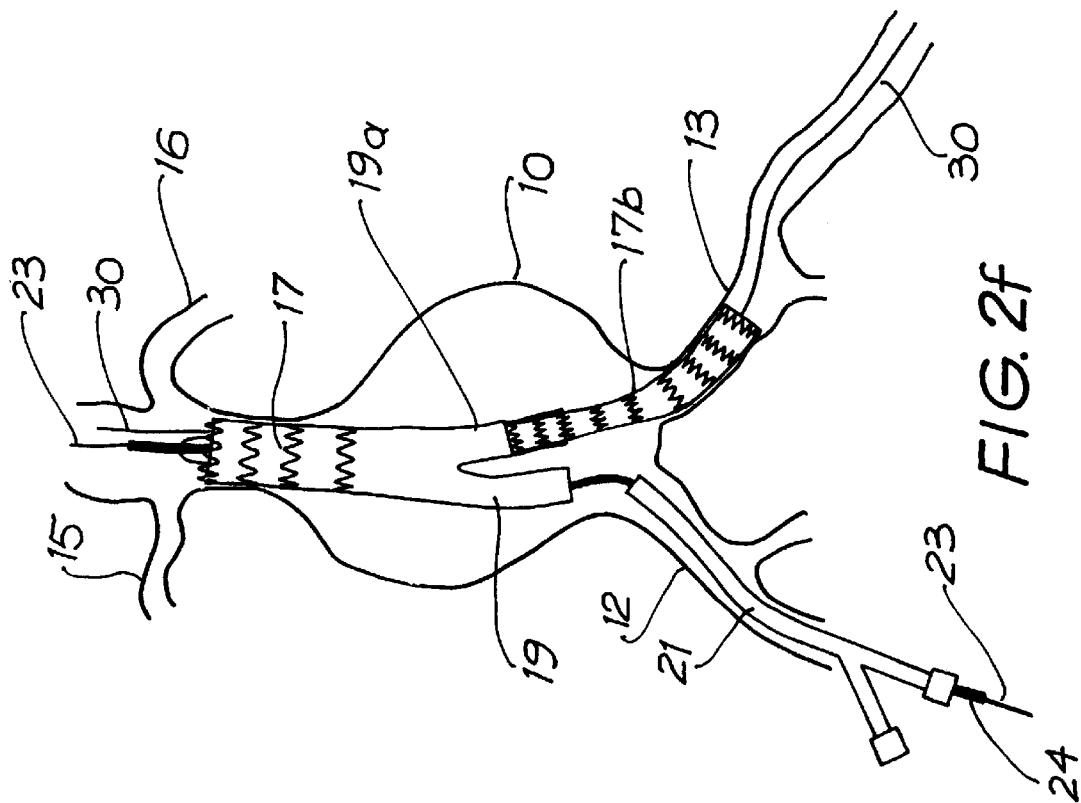
Figure 2E:
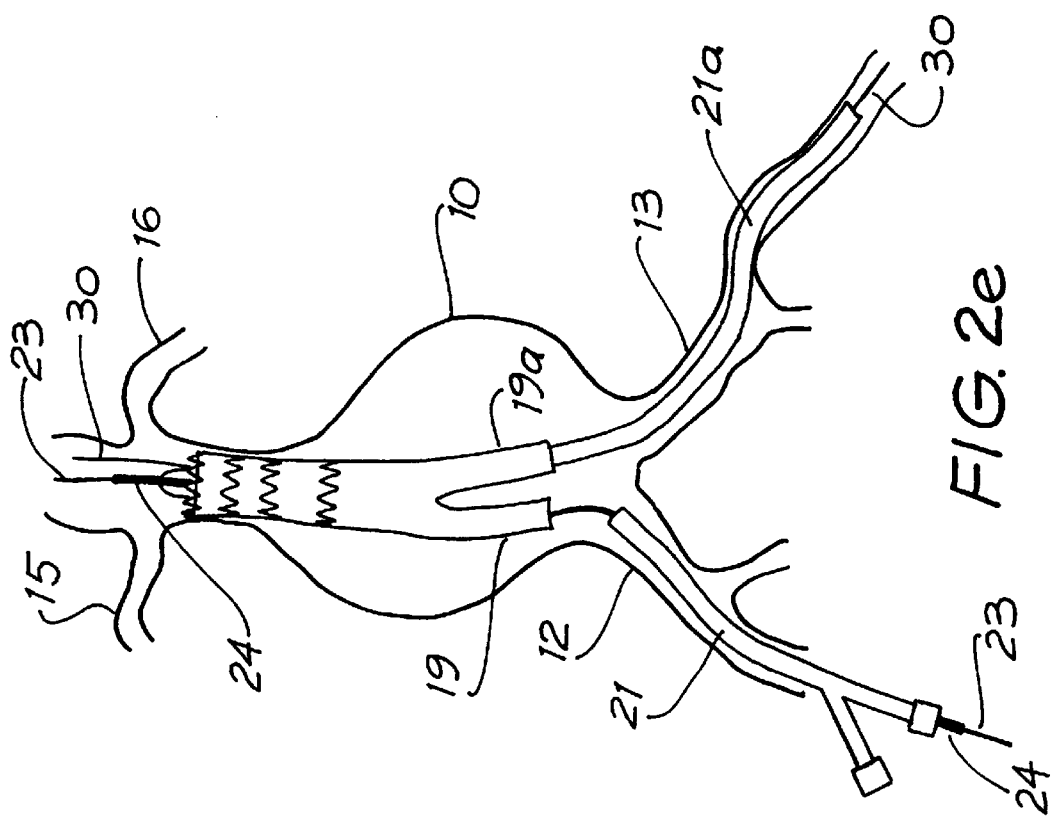
Figure 2H:
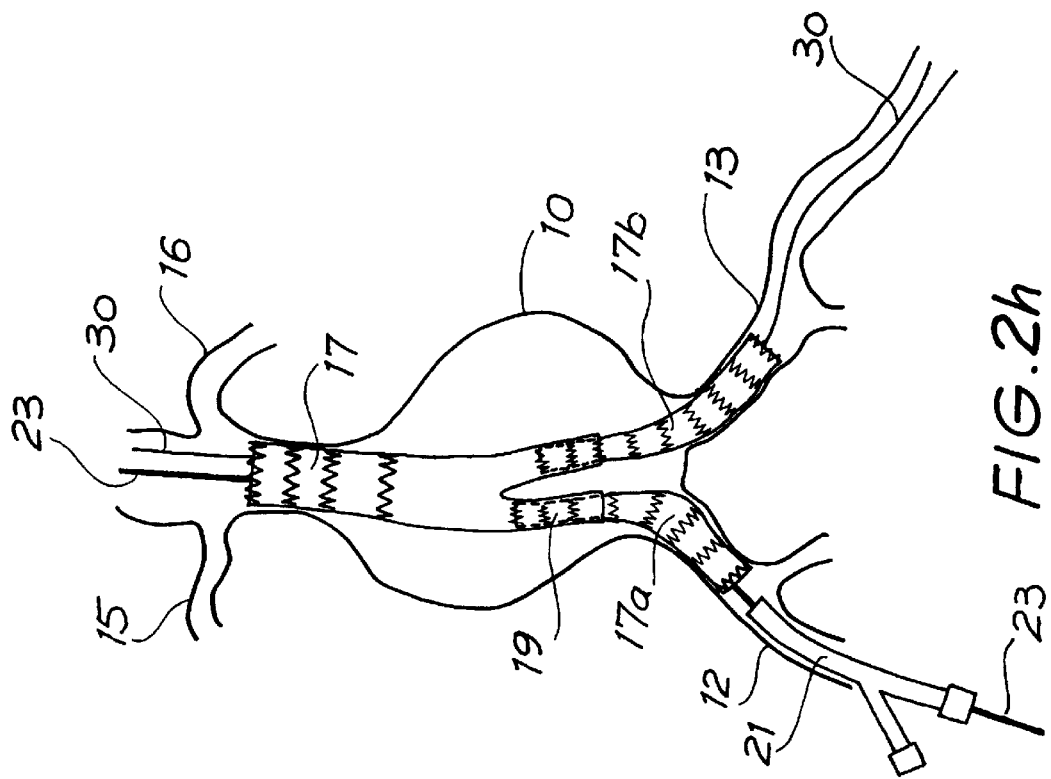
Figure 2G:
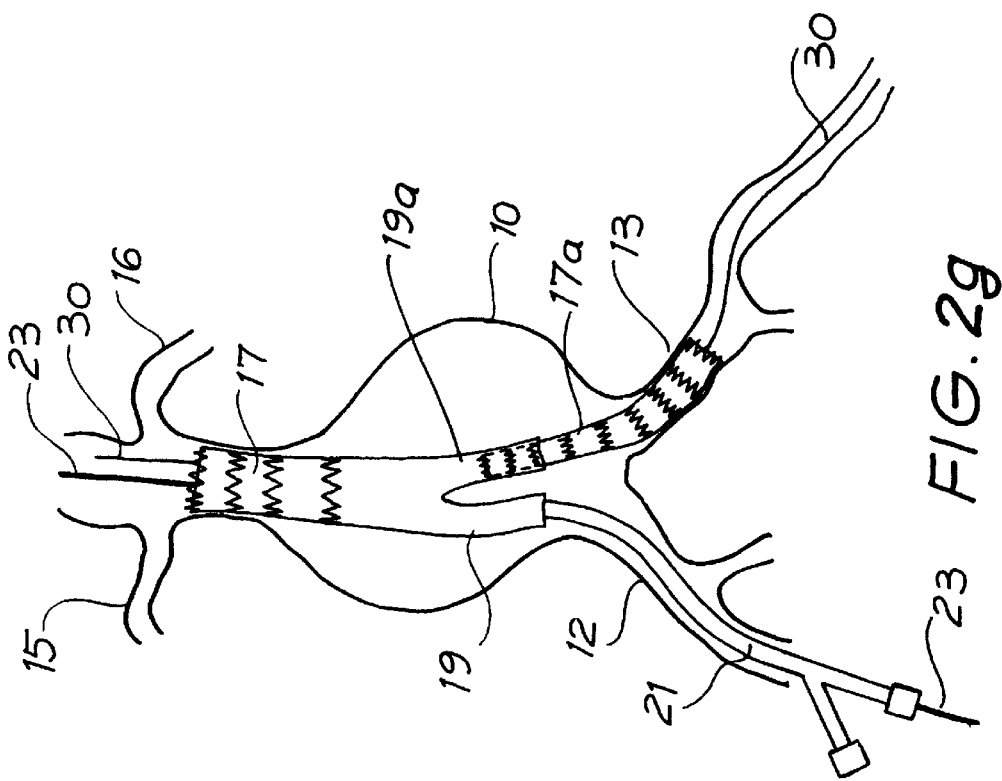
Figure 4:
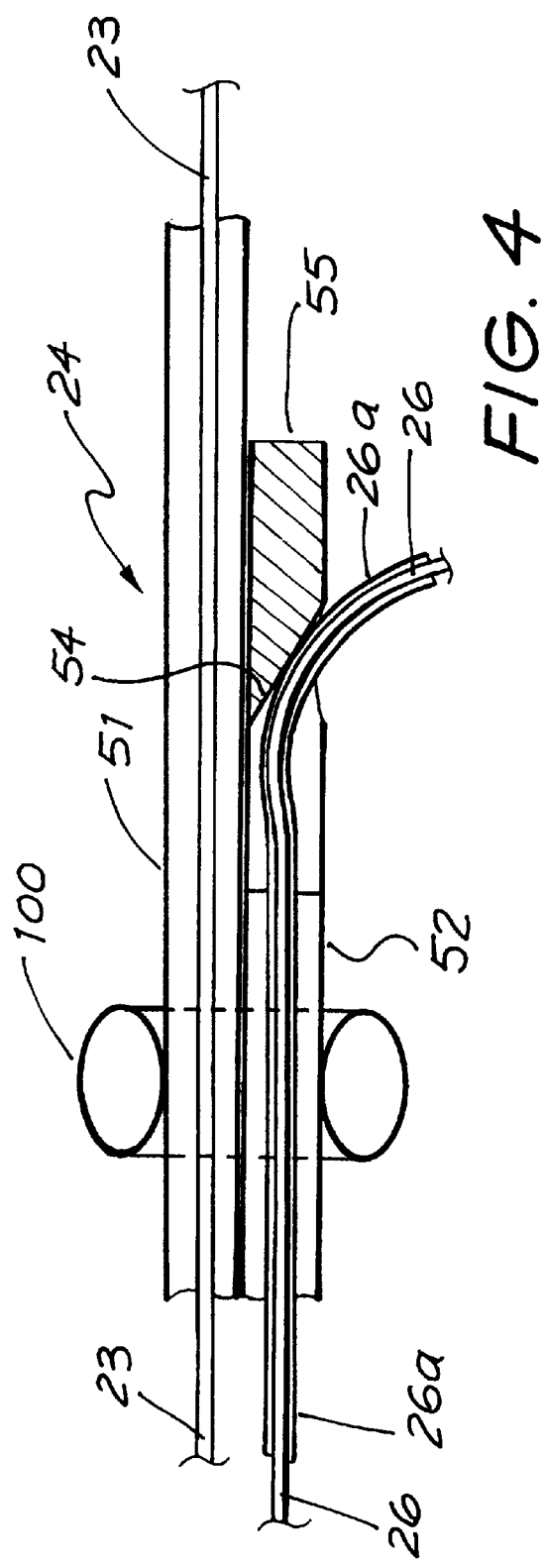
FIG. 4 is a cross-sectional view of the end portion of FIG. 3.

The catheter 26a can be deployed through the aperture 50 as desired by the physician. The guidewire 26 can then be guided through the catheter 26a and into the left iliac artery 13 as is depicted in FIG. 2c. As is depicted in FIG. 4, the catheter 24 can also have an inflatable balloon 100 proximate the end 55 of the first tubular member 52. The balloon 100 can be inflated once the catheter 24 is in place to further hold the catheter 24 in the appropriate position and block the right iliac artery 12 so ensuring blood flow is directed down the left iliac artery 13 as the guidewire 26 is being guided through the left iliac artery 13.

Rather than normally assuming a curved or angled configuration proximate its tip, it can be readily envisaged that the catheter 26a could be modified from that depicted such that it has the features of the catheter 24 or the catheters 60 and 70 described in more detail below. For example, the catheter 26a could also have first and second elongate tubular members, with the second elongate tubular member disposed over the guidewire 26 and the first tubular member having directing means to direct a further guidewire passing therethrough in a desired direction. Such a catheter could be used in the present application where it is necessary to eventually direct a guidewire from the left iliac artery 13 into the corresponding left femoral artery.

Figure 7:
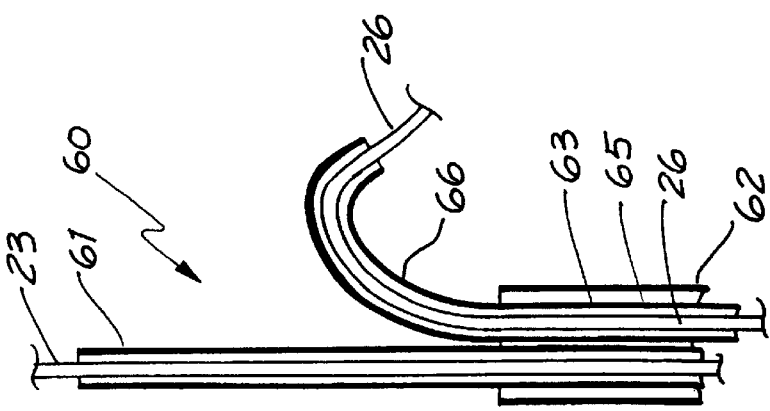
FIG. 7 is a cross-sectional view of the end portion depicted in FIG. 6.
Figure 6:
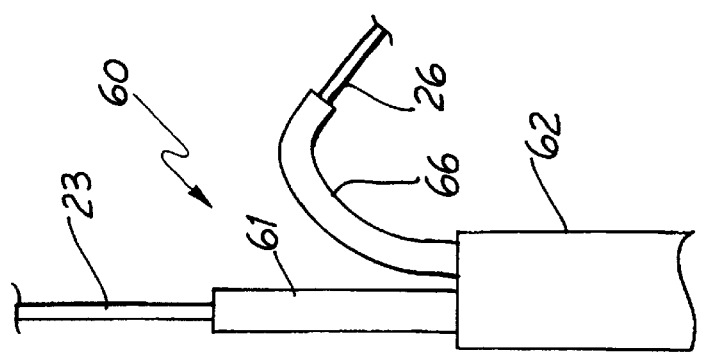
FIG. 6 is a further view of the end portion of FIG. 5 with the sleeve retracted relative to the end portion.
Figure 5:
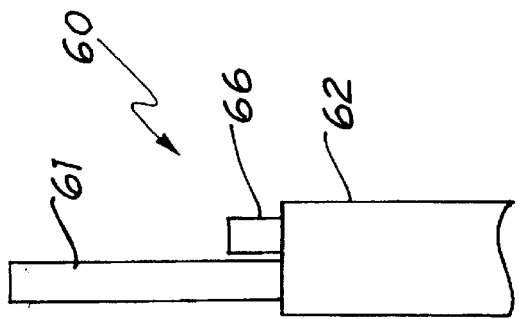
FIG. 5 is a side elevational view of the end portion of a second embodiment of an intraluminal catheter according to the present invention.

Alternative embodiments of the intraluminal catheter according to the present invention are depicted in FIGS. 5–8. One alternative is depicted generally as 60 in FIGS. 5–7. The catheter 60 has a first elongate tubular portion 63 having a main portion 65 that normally assumes a relatively straight configuration and an end portion 66 (fabricated from a shape memory material) that normally assumes a curved configuration. While the end portion 66 is depicted as normally assuming a curved configuration, it can be readily envisaged that the end portion 66 could be preformed with an angle if this more suited the application of the catheter 60. The catheter also has a second elongate tubular member 61 that acts as a support means for the catheter 60 by being able to be slid over a guidewire, such as the stiff guidewire 23 used in the depicted example at FIGS. 2a–i. The catheter further has a sleeve 62 that is relatively movable along the catheter 60 between a first position where it surrounds the first and second tubular members 63,61 (such as is depicted in FIG. 5) and a second retracted position where the end portion 66 is free to assume its normal configuration (such as is depicted in FIGS. 6 and 7). If used in the placement of an intraluminal graft such as is depicted by FIGS. 2a–i, the graft 17 is packaged about the catheter 60 such that the end portion 66 is positioned just above the bifurcation 17c. Once the catheter 60 is in the desired position in the aorta 10, the graft 17 is deployed as described above. The sleeve 62 is then retracted relative to the end portion 66 thereby allowing the end portion 66 to assume its normal curved configuration. The guidewire 26 is then guided through the first tubular member such that it emerges from the end portion 66 in the desired direction into the left iliac artery 13.

While only the guidewire 26 is depicted being guided through the end portion 66 of the catheter 60 in FIGS. 5–7, it can be readily envisaged that a supplementary catheter, such as the supplementary catheter 26a, could be used in association with the catheter 60 as was described in relation to catheter 24.

Figure 8:
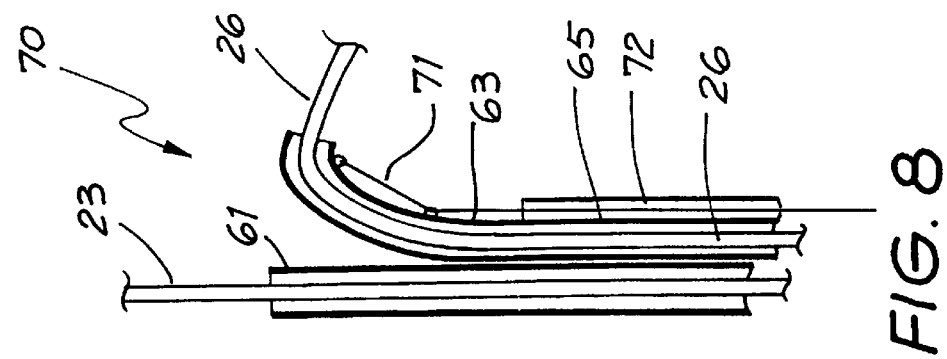
FIG. 8 is a cross-sectional view of the end portion of a third embodiment of a intraluminal catheter according to the present invention.

The catheter generally depicted as 70 in FIG. 8 has many of the features of the catheter 60 except that the orientation of the end portion 66 relative to the main portion 65 is controlled by a physician manipulating the control wire 71 which is secured to the end portion 66 and is fed back through a further lumen 72 in the catheter 70. As with the other depicted embodiments, the guidewire 26 on being guided through the end portion 66 is directed in a desired direction towards the left iliac artery 13.

The guidewire 26 is preferably comprised of a non-kinking nitinol alloy material. If desired, the guidewire 26 may have proximate its tip a flow impedance device such as, an inflatable balloon 74 (see FIG. 2c) (which can be inflated by passing a fluid, such as air, down a lumen in the guidewire 26), which serves to help the guidewire 26 to be carried and directed by blood flow into the left iliac artery 13.

As described above, if necessary, a further catheter having the features of one of the embodiments of the invention described herein can be fed over the guidewire 26 to assist in the placement of a further guidewire into another vessel branching off the left iliac artery 13.

One advantage of the present invention, apart from it providing better control over the placement of a guidewire into a vessel, is that the catheter when positioned in a vessel over the main guidewire 23 provides appropriate support for the supplementary guidewire 26 as it is guided through the catheter and directed into the branching vessel.

Once the guidewire 26 is correctly placed in the left femoral artery, a cutdown can be effected to that femoral artery which is cross-clamped and an arteriotomy effected. If the guidewire 26 has been guided fully into the contralateral femoral artery, the guidewire 26 is simply recovered by drawing the guidewire 26 through the incision or puncture made in the artery. If the guidewire 26 has not been guided fully along the femoral artery, a snare or similar device can be introduced through the contralateral femoral artery to grab the guidewire 26 and draw it back to the puncture or incision site for retrieval. Once the guidewire 26 is retrieved, a catheter 27 is then fed through the contralateral femoral artery up the guidewire 26 until it is within the first graft 17 and reaches at least the top of the contralateral tubular extension 19a. The guidewire 26 is then withdrawn and a stiffer guidewire 30 inserted through the contralateral femoral artery into the catheter 27. The catheter 27 is then removed and a catheter sheath 21a, and dilator are introduced over the stiff guidewire 30 (see FIG. 2e).

Figure 10:
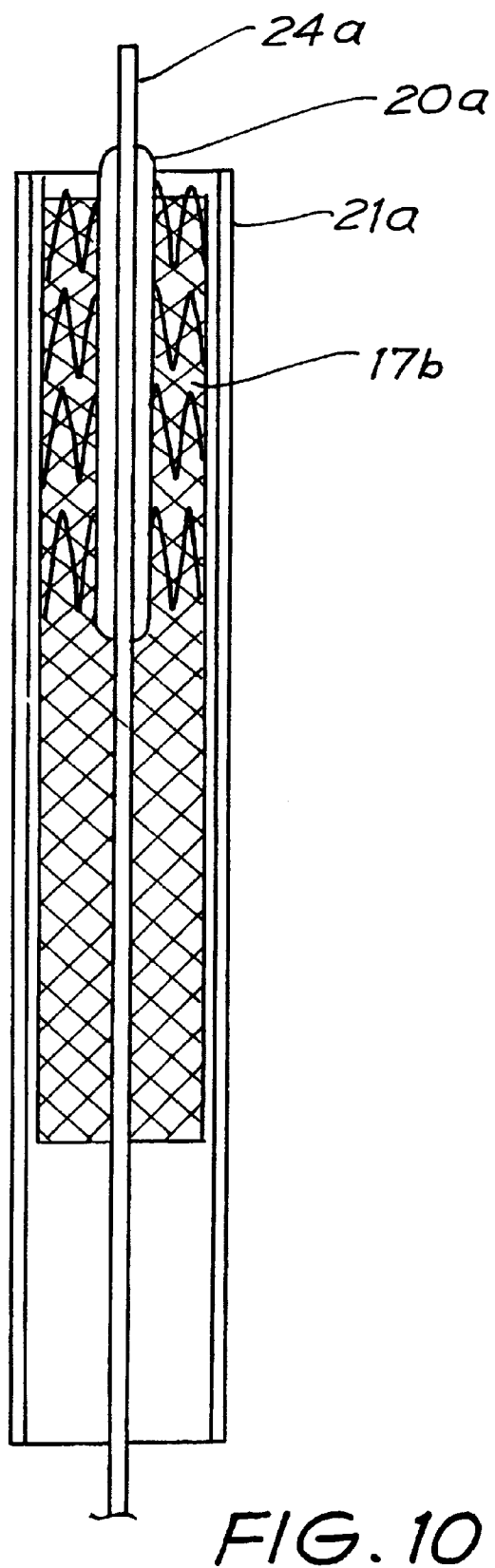
FIG. 10 is a vertical sectional view of one embodiment of a tubular graft mounted over a delivery catheter for use in the method depicted in FIGS. 2a–i.

A second balloon catheter 24a, such as is depicted in FIG. 10, on which is packaged a second tubular graft 17b is then introduced through catheter sheath 21a until its upper end is well within the contralateral tubular extension 19a at its upper end and within the left iliac artery 13 at its lower end. The balloon 20a on the catheter 24a is inflated such that the upper end of graft 17b is frictionally engaged with the contralateral tubular extension 19a (see FIG. 2f). The inflation of the balloon 20a on the catheter 24a supports the graft 17 during the withdrawal of the first balloon catheter 24 through the right iliac artery 12. The balloon 20a is then deflated and the catheter 24a maintained in place to provide continued support for the grafts 17,17b in the aorta 10 while the third graft 17a is positioned.

The catheter sheath 21a is then removed (see FIGS. 2f and 2g) and a third balloon catheter, on which is packaged a tubular graft 17a, (the third balloon catheter can be identical to that depicted in FIG. 10) is introduced into the sheath 21 on guidewire 23. It is advanced until its upstream end is within the ipsilateral extension 19 and, following partial withdrawal of the sheath 21, is then deployed. A third graft 17a positioned on the third balloon catheter is thus urged at its upstream end into contact with the ipsilateral extension 19 and its downstream end into contact with the right iliac artery 12 (see FIG. 2h).

Figure 2I:
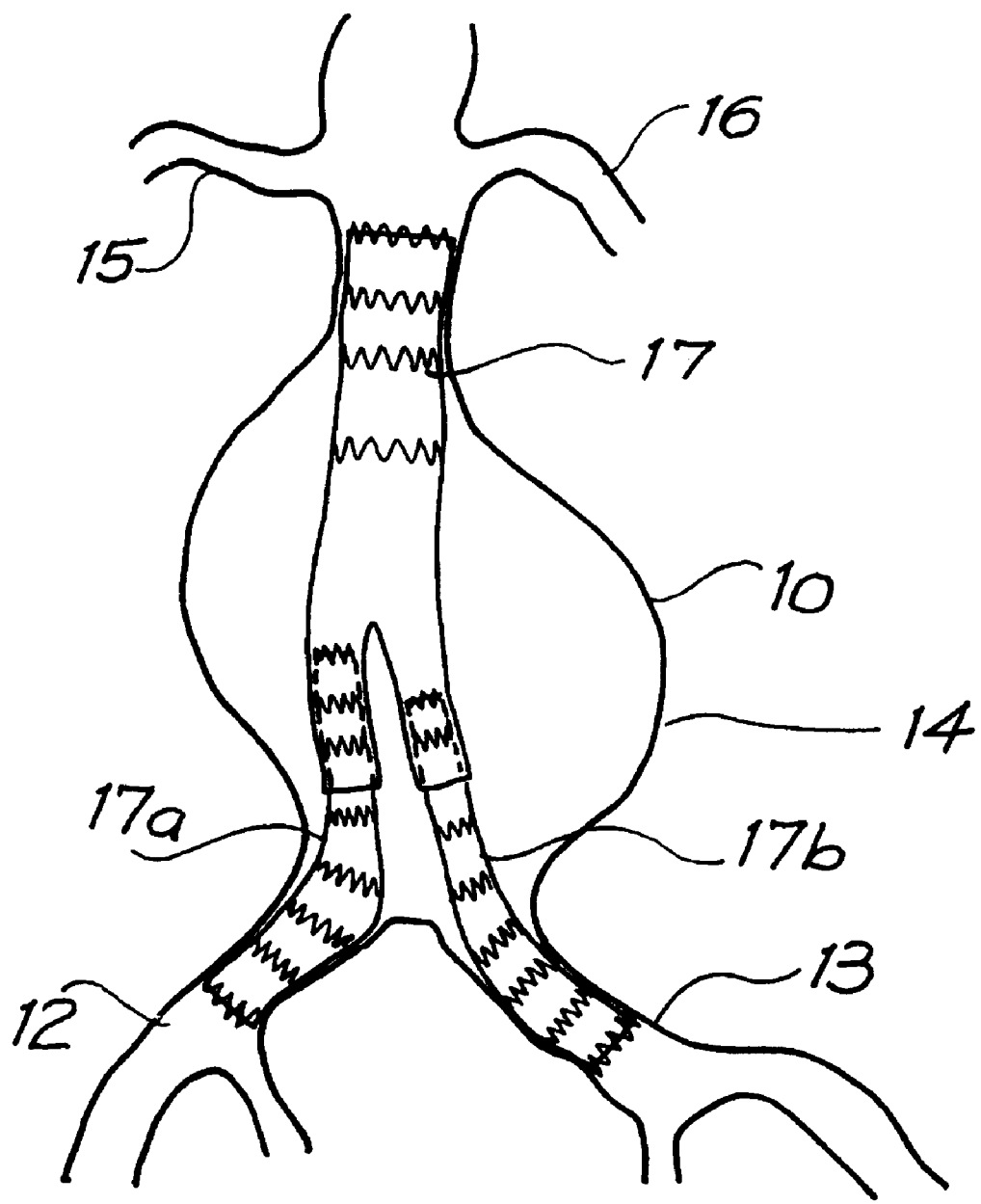

The stiff guidewires 23 and 30 are now withdrawn and the contralateral incision or puncture sutured. A second angiographic examination now takes place and if the grafts 17, 17a and 17b are correctly placed and functioning, the haemostatic sheath 21 is withdrawn and the right femoral incision sutured (see FIG. 2i). The result is a functioning trouser graft bridging an aneurysm as is depicted in FIG. 2i.

The operation may be carried out using a general anaesthetic, an epidural anaesthetic, or in suitable cases, using only a local anaesthetic.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A guidewire deflecting catheter system, comprising:
    a deflecting catheter defining an axis and an axially extending primary guidewire lumen;
    a first elongate tubular member defining a lumen separate from the primary guidewire lumen and having a flexible distal end, the first tubular member extending axially substantially along the length of the primary guidewire lumen in a first, undeflected state, the distal end of the first tubular member being relatively moveable with respect to the primary guidewire lumen so as to deflect transversely with respect to the catheter axis to a second, deflected state;
    a primary guidewire positioned within the primary guidewire lumen; and
    a deflecting guidewire relatively more flexible than the primary guidewire and sized to be positioned through the lumen of the first tubular member and be deflected through the distal end in its second, deflected state and thereby project out of the distal end transversely with respect to the catheter axis.

2. A system for delivering a guidewire to a contralateral leg of a bifurcated graft, the bifurcated graft having a tubular main portion branching into two tubular extensions, an ipsilateral extension and a contralateral extension, at a bifurcation point, the system comprising:
    a catheter defining an axis and an axially extending primary guidewire lumen, the catheter including a first elongate tubular member defining a lumen therein and having a flexible distal end, the flexible distal end being operable between a first, undeflected state wherein the first elongate tubular member extends axially substantially along the length of the primary guidewire lumen, and a second, deflected state wherein the flexible distal end is deflected transverse to the catheter axis;
    a primary guidewire that can be positioned through the bifurcated graft via the ipsilateral extension, the catheter also capable of being positioned within the bifurcated graft over the primary guidewire with the distal end of the first tubular member adjacent the bifurcation point; and
    a deflecting guidewire relatively more flexible than the primary guidewire and being sized to be positioned through the lumen of the first tubular member in its second, deflected state to thereby project out of the first tubular member distal end transversely with respect to the catheter axis and into the contralateral extension.

* * * * *